United States Patent [19]

Sievert et al.

[11] Patent Number: 5,197,940
[45] Date of Patent: Mar. 30, 1993

[54] LOCAL APPLICATION TUMOR TREATMENT APPARATUS

[75] Inventors: Chester E. Sievert, Mahtomedi, Minn.; Robert D. Tucker, North Liberty; Stefen Loening, Iowa City, both of Iowa

[73] Assignee: Hypertherm Corp., Mahtomedi, Minn.

[21] Appl. No.: 471,498

[22] Filed: Jan. 29, 1990

[51] Int. Cl.$^5$ ............................................. A61B 17/52
[52] U.S. Cl. ......................................... 600/9; 600/12; 600/13; 600/8; 128/402
[58] Field of Search ............... 128/399, 401, 402, 403, 128/783, 804, 377, 378; 606/27, 28; 600/9, 10, 12, 13; 336/62

[56] References Cited

U.S. PATENT DOCUMENTS

| | | | |
|---|---|---|---|
| 435,376 | 8/1890 | Brown | 600/13 |
| 477,495 | 6/1892 | Waite | 128/377 |
| 485,238 | 11/1892 | Thomas | 128/377 |
| 561,448 | 6/1896 | Slater | 600/13 |
| 636,093 | 10/1899 | Whitfield | 600/13 |
| 849,653 | 4/1907 | Bachelet | 128/377 |
| 1,120,964 | 12/1914 | Neel | 600/13 |
| 1,164,356 | 12/1915 | Kaiser | 600/9 |
| 1,375,050 | 4/1921 | Krauer | 600/13 |
| 1,418,903 | 6/1922 | Benson | 600/13 |
| 3,653,385 | 4/1972 | Burton | 128/399 |
| 4,106,488 | 8/1978 | Gordon | 128/399 |
| 4,316,453 | 2/1982 | Harrison | 128/804 |
| 4,537,181 | 8/1985 | Shalhoob et al. | 600/9 |
| 4,574,782 | 3/1986 | Borelli | 600/10 |
| 4,590,922 | 5/1986 | Gordon | 128/401 |
| 4,874,916 | 10/1989 | Burke | 336/62 |
| 4,923,437 | 5/1990 | Gordon | 128/401 |
| 4,983,159 | 1/1991 | Rand | 600/9 |

OTHER PUBLICATIONS

The RF Thermoseed-A Thermally Self-Regulating Implant for the Production of Brain Lesions, Burton et al., Mar. 1971, IEEE Transactions on Bio-Medical Engineering pp. 104-109.

Primary Examiner—William E. Kamm
Assistant Examiner—Robert L. Nasser, Jr.
Attorney, Agent, or Firm—Kinney & Lange

[57] ABSTRACT

Disclosed is apparatus and method for treating prostate tumors. The apparatus includes a platform on which the patient may be seated. An electromagnetic coil is disposed beneath the platform and creates a field that acts on thermoseeds placed in the tumor. The method includes inductively heating the thermoseeds which heat the tumor cells to a temperature of between 45° and 50° C.

8 Claims, 2 Drawing Sheets

LOCAL APPLICATION TUMOR TREATMENT APPARATUS

FIELD OF THE INVENTION

The present invention relates to medical treatment and more particularly to local treatment of tumors either cancerous or benign on an out patient basis.

BACKGROUND OF THE INVENTION

The present invention contemplates equipment for treatment of various localized tumors such as prostate, rectal, cervical or uterine. The term "tumor" as used herein refers to any abnormal tissue growth. In fact, the invention may be used for any temperature sensitive tumor. The present invention will be described with regard to a typical type of tumor suitable for treatment with the equipment of the present invention, namely, prostate cancer.

Prostate cancer is the second most common cancer in males in the United States, and the third most common cause of male cancer death. In 1986, an estimated 90,000 men in the US were diagnosed with prostate cancer, and 26,100 death from the disease were estimated to have occurred.

Age has a major impact on the incidence of prostatic cancer. The disease is uncommon in men younger than age 50, but the incidence increases sharply to more than 1,000 per 100,000 man-years for American males age 85 and over. The average age of prostate cancer patients at the time of diagnosis is 73 years. For males over the age of 75, mortality due to prostate cancer is exceeded only by lung cancer. Relative to other forms of malignancy, this disease accounts for 21 percent of newly diagnosed cancers in males and 11 percent of cancer deaths.

Many factors are involved in choosing treatment modes for the individual patient. Those factors are patient age and anticipated life expectancy, associated medical problems, sexual potency, potential complications of therapy, and, ultimately, consideration for quality of life with and without therapy.

In choosing appropriate treatment options cost factors have been largely ignored in the past. The cost, including physician fees, of perineal prostatectomy is substantial with typically 8.0 hospitalization days required. The delivery of external radiation therapy for localized prostate cancer according to the present invention may be a 6-weeks-course on an outpatient basis. Treating patients with the method of the present invention, e.g. hyperthermia delivered on an outpatient basis would lead to a reduction of hospital days associated with surgery. In the context of radiation therapy effective hyperthermia can enhance the effect of radiation and result in a higher local cure rate.

Traditionally radical prostatectomy has been widely employed on otherwise healthy men with clinical Stage A or B and occasionally small Stage C lesions. Limitations in success in treatment stem from inaccurate clinical staging which fails to predict extraprostatic carcinomatous spread prior to surgery.

Despite numerous refinements in surgical technique, the role of prostatectomy for patients with histological evidence of extracapsular disease remains uncertain. Attempts to treat residual cancer following incomplete resection evidenced by histological demonstration of capsular penetration, involving surgical margins or seminal vesicels, have focused primarily upon external beam irradiation techniques administered in the period following total recovery from surgery.

Radiotherapy, like surgery, offers a patient the possibility of local-regional control of prostatic carcinoma. External beam radiation has generally been given to the prostate in doses of 5,500 to 7,000 rads. Perez et al. have reported a failure rate of 18.5% in patients who received 7,000 rads to the prostate. Cupps and associates found a 14% rate of local recurrence by digital examination in patients who had received external-beam radiation; in stage B disease, they observed a 20% combined local and systemic failure rate, whereas the combined failure rate for stage C disease was 49%. Lupu and associates have reported a 32% five-year local failure rate for stage C lesions treated with external radiation alone. Gibbons et al. have found a 92% local clinical control rate for stage C carcinoma of the prostate with external radiation alone, but they define local control as lack of requirement of further surgery for obstruction or bleeding. Other investigators have observed that postradiation biopsy continues to be positive for residual tumor in 40% to 70% of patients treated with external-beam radiation. Unfortunately, the determination of local clinical control has in the past relied on digital examinations and not on sensitive serum markers and ultrasonic rectal follow-up checks. Local tumor recurrence or persistence has nevertheless been associated with a higher incidence of systemic failure. These findings would lead to suggest modalities to increase the effectiveness of radiation with the use of adjunct hormonal or chemotherapy treatment or with the use of hyperthermia.

Interstitial radiation therapy with iodine isotope (I-125) has been reported to carry a 16% incidence of local failure in patients with stage C disease followed five years. Scardino et al., however, observed an incidence of positive postradiation biopsy of 50%. Local tumor recurrence using a combination of radical surgery and interstitial gold isotope (AU-198) has been reported in the range of 4% to 8%.

Since 1866, when Busch published the first scientific report of a regression of a histologically proven sarcoma following an attack of high fever caused by erysipelas, many authors have reported the disappearance or regression of tumors by hyperthermia therapy.

GENERAL DESCRIPTION OF THE PRESENT INVENTION

Hyperthermia can be achieved through an induced temperature of more than 41.4° C., within living organism or a part of it, where the physiological temperature regulation of the body is partially overcome with the aim of achieving a therapeutic effect.

Malignant cells, whether in tissue culture or in experimental animals, are more sensitive to heat than normal cells, with chromosomal aberrations induced only when the cells are heated in S-phase. The degree or extent of heat damage to the replication process is dependent not only on time and temperature of the heat shock given to the cells, but also on the intrinsic thermal sensitivity of the cells. Higher temperature minimize development of thermotolerance.

The direct effects of thermal damage are related to 1) a reduced rate of transport of amino acids and thymidine into cells following heating; 2) decreased binding of epidermal growth factor in Rat-1 cells and decreased binding of insulin to CHO cells; 3) leakage of polyamines from heated cells and 4) potentiation of heat killing, inhibition of DNA synthesis, and loss of cellular polymerase beta activity by membrane active agents.

The further effect of heating is related to increased permeability of cell membrane, leading to a subsequent change in the intracellular ionic environment. This may cause the absorption of cytoplasmic and nuclear proteins to the DnA in the nucleus and also effect numerous enzymatic reactions.

The phenomenon of thermotolerance is a complication in the clinical use of hyperthermia. Riabowol suggest that synthesis of a small group of highly conserved proteins in response to the first thermal shock exhibit significantly higher survival rates to a second, otherwise lethal damage. A correlation exists between the expression and decay of thermotolerance and the induction, accumulation, and degradation of heat shock protein. Those referred to as the hsp70 family are the most conserved and the best characterized. In most mammalian cells there are two prominent forms of hsp70, an abundant constitutive member, hsp73, and a highly stress-inducible member, hsp72. In response to heat shock, these proteins are rapidly sequestered in the nucleolus involved in the assembly of small ribonucleoproteins and preribosomes. During recovery from heat shock, the 70k hsp accumulates in the cytoplasm where a portion colocalizes with ribosomes and polysomes. At lower temperature of around 42° C., thermotolerance is induced during the heating period after an exposure of around 2 or 3 hours. By contrast at higher temperatures of around 45° C., thermotolerance cannot be produced during the heating, and it is delayed by 8 hours or so after the heating period. The time taken for cells that have become thermotolerant to revert to their normal sensitivity, may take as long as 100 hours. The greater the degree of damage, the greater is the time for the thermotolerance to decay. In addition, the faster the increase of temperature, the higher the temperature, and the longer the time of exposure, the smaller are the number of thermotolerant cells found within cultured cell lines.

Hyperthermia generally decreases blood flow in tumors, frequently irreversibly, however, blood flow is sometimes restored 1-3 days after application of heat, depending on the tumor model. Upon heating, the intratumor environment becomes acidic, hypoxic, and nutritionally deprived due probably to vascular damage. Such a suboptimal environment in the heated tumors potentiates the response of tumor cells to hyperthermia, inhibits the repair of thermal damage, and also interferes with the development of thermal tolerance. Heating and damage of tumor can be expected only if heat is preferentially delivered to the tumor or if heat dissipation by blood flow is slower in the tumor than in the surrounding normal tissue. Tumor vasculature, however, is less able to dissipate heat and more likely to be damaged when treated with hyperthermia. Systemic temperature elevation during regional hyperthermia results from the dissipation of large quantities of thermal energy through circulation. This is generally an undesirable by-product of regional hyperthermia, which may seriously compromise adequate delivery of thermal treatment.

Electromagnetic (microwave) and ultrasonic methods can be used to heat tissue locally. At high temperature, e.g. above 45° C., heat begins to indiscriminately damage both normal and cancer cells. This limits temperature rise in tissue to a narrow therapeutic range, to avoid both enhancement of the active growing tumor edge and damage to normal cells. Using this method it is difficult to selectively act on the desired tissue, e.g., microwave heats everything in the vicinity. Also, hot and cold spots are a problem with microwave.

Temperature distribution within tumors treated by external methods even in annular phased array systems is difficult to achieve. Thermal mapping can be achieved using multisensor temperature probes, but is an additional invasive activity.

Another limiting factor of the external heating techniques is the excessive heating of normal surrounding tissues, usually with associated patient discomfort and/or pain. Mucosal necrosis of the urinary bladder, due to the high thermal sensitivity of the urothelium, has been reported. This necessitates bladder cooling in hyperthermia treatment of patients with pelvic tumors. Using rectal applications, mucosal damages also have been reported.

Ultrasound beams, although focusable and sufficiently penetrating in soft tissues and fluids, are limited in their applicability due to their strong absorption by bone and their high reflection by air-filled cavities.

Interstitial techniques, on the other hand, produce heat by means of devices implanted directly into the diseased area. Heating is thereby confined to the target volume and is affected little by surrounding tissues or air cavities. The only drawback of this approach is the invasiveness. Such invasive methods of heating tumors include implanted metallic electrodes and microwave antennas. Each time the electrode is inserted it serves as a track for infection. Also, anesthesia is required for each insertion.

Electromagnetic field focusing (EFF) is capable of producing intense heat at a given point in tissue. If biological tissue is placed in an electromagnetic, field, eddy currents are induced to flow within the tissue. The tissue is not heated until it is grounded by a conductor, e.g. needle electrode, at which time a sharp and intense convergence of the eddy currents, at the point of contact of the electrode to tissue, produces heat.

The present invention is a less invasive technique and involves the implantation of thermoseeds. These seeds are implanted and then may be inductively heated by a magnetic field. A needle is used to implant thermoseeds. The biocompatable thermoseeds, after insertion, remain in place over an extended period of time. The seeds are heated by induced current flow without electrical connection such as that needed in the EFF-method. As the magnetic field strength needed to heat the implanted seeds is low (less than 100 oersteds), there is no adverse short term or long term tissue effect. Thermoseeds are very small and less invasive than other techniques. Thermoseeds once inserted have no connection with the outside world.

Thermoseeds can be made from materials having a ferromagnetic to paramagnetic transition (Curie point) at the desired temperature. As the Curie point is approached, the implants begin to lose their ferromagnetism, and thereby their rate of heat production is decreased and temperature becomes static. The automatic regulation offered by this technique leads to better temperature homogeneity. These are the so called self-regulating thermoseeds. The rate at which heat is produced by a cylindrical thermoseed depends on its radius, length, magnetic permeability, and on the intensity and frequency of the applied induction field. The rate of heat production goes up if any of these parameters are increased. Furthermore, the heating power depends on the orientation of the implants with respect to the magnetic induction field. Thermoseeds must be oriented properly, e.g. with the direction of the magnetic field in order to function properly. Although deviations of up to 45 degrees are acceptable, larger angles of misalignment lead to a substantial drop in heating power.

Self regulating thermoseeds have theoretical advantages in localized and accessible tumor systems. The prostate fulfills these criteria, and has immense clinical importance, because of benign enlargement and malignant potential.

When the interface between the tumor tissue and surrounding normal tissue is kept at 50° C. or less, damage to the surrounding tissue is minimal and reversible as shown by testing in animal models. Total cancer cell necrosis was found to occur in all animals at 50° C. maintained for 10 to 15 minutes. A thermoseed consisting of 70.4% nickel and 29.6% copper gave consistent temperatures of 50.1° C., although other seeds have also been used, e.g. palladium - copper, nickel - silicon, iron oxide, and manganese oxide. Suitable seeds would also include coated seeds, e.g. Teflon ® PTFE fluorocarbon coated seeds. The thermoseed may be of a radioactive material such as a coating of radioactive gold on nickel/copper. This would provide a dual function treatment.

Migration of seeds is not a problem, if similar size seeds are used as for interstitial radiation therapy. Desirably, the seeds are about 3 or 4 centimeters in length. Seeds tend to migrate if they are 5 cm or larger in length. Calorimetrica measurements of seeds of 0.9 mm diameter showed that they should not be shorter than 7 mm in length. The spacing of seeds should not exceed 1 cm to effect uniform heating.

Temperature elevations produced by thermoseeds strongly depend on blood flow. For example, in tisuse having a blood perfusion rate of 20 times that of resting muscle, the coldest point in a thermoseed array with 1 cm spacing would reach only 30° C., even if the thermoseeds maintained the rather high temperature of 50.1° C. Fortunately, the blood flow in a tumor is usually lower than in normal tissue counterparts.

Undesirable heating of metal objects in a magnetic field is a matter of concern. Small foreign elements such as surgical clips and permanently radioactive seeds will not be a problem, provided their shape, diameter and length are smaller than that of the thermoseeds. However, large metal objects, such as prosthesis and pacemakers, could limit the applicability of the present thermoseed method with certain patients. Nevertheless, the present invention is less prone to problems of this nature since the field is localized and focused.

Clinical use of hyperthermia is based on the following observations: 1) hyperthermia is a potent modifier of the response of tumors to radiation and can be tumoricidal per se; 2) hyperthermia enhances the killing of tumor cells by selected chemotherapy agents; 3) hypoxia does not protect cells against the effects of hyperthermia as it does against x-rays, and; 4) when subjected to local hyperthermia, solid tumors act as a heat reservoir because of their poor blood flow. Since tumors are unable to augment blood flow in response to thermal stress, they are more vulnerable to heat damage than the surrounding normal tissue with its efficient vascular cooling system, which rapidly adjusts to local heating burden.

Using the annular phased array system, toxicity to hyperthermia has been observed in 30% of patients treated. The so-called post-hyperthermia stress syndrome consisted of sudden rise in systemic temperature and pulse rate, and chills within a short time of hyperthermia with all the symptoms subsiding in less than 24 hours.

In the present invention, an array of ferromagnetic seeds are implanted in the tumor. The patient is placed in a magnetic induction field which produces heat within the seeds. The absence of any electrical connecting wires between the implants and the power source makes this heating method very practical. Human patients tolerated hyperthermia with mild sedation.

While the present invention is disclosed with respect to prostate cancer, it may be used with various other tumors. Clinical studies have demonstrated the efficacy of hyperthermia with radiotherapy in the treatment of adenocarcinoma of the breasts. About half of the lesions treated with radiotherapy alone were controlled, while all of the lesions treated with the combination were controlled at one year. When these patients were followed for up to three years, of those controlled by irradiation alone, failure was observed regularly at the three month follow-up visits. The implication of this failure rate is that half of the controlled lesions will have recurred at two years. In sharp contrast, only one lesion treated with hyperthermia-radiation combined recurred. It appears that 70% have complete eradication of their local lesion with the use of combination of hyperthermia with radiation therapy.

Since in addition to man only the dog is known to develop benign prostatic hyperthropy (BPH) spontaneously, the experimental data available on BPH was obtained in dogs.

The high temperatures achieved in dog studies with BPH were necessary to overcome the vasculatory cooling system of normal tissue. Extreme temperatures are not necessary in the treatment of tumors, as they act as a heat reservoir and are unable to augment blood flow in response to heat. This difference allows the production of high temperatures in tumors while minimizing damage in normal tissue.

The sensitivity of the normal prostate tissue to hyperthermia was also examined in a rabbit model. Using a transrectal probe, microwave-induced heating was applied to the prostate at 42.6 to 43° C. for 30 minutes. Histological examination was performed after one day to three months of hyperthermia treatment. Although hyperthermia effects were noticed in the rectum, no detectable pathological damage of The similarities of these rabbit and dog models to the human disease have been documented with regard to hormonal, chemotherapeutic, and radiation therapeutic manipulations.

Some researchers are using an electromagnetic hyperthermia system with rectal cooling to treat patients with BPH and prostatic cancer. Intraprostatic temperatures of 43 to 43.5° C. are achieved 10 to 15 minutes after initiation of therapy. Patients received 6–10 treatments during the study. Hyperthermia was applied three times a week. In patients with prostatic cancer, radiation preceding hyperthermia was the preferred treatment combination. Local control of prostate cancer was achieved within the reported follow-up period. All patients treated with hyperthermia for BPH had resolution of their voiding problems. Patients were evaluated during hyperthermia treatment and at 3 and 6 month intervals. Each case was evaluated by transrectal ultrasonography, residual urine, uroflowmetry, rectoscopy and blood/urine analysis. Furthermore, investigators indicated that prostatic biopsy in the group with advanced cancer of the prostate showed downgrading or even disappearance of the tumor.

A series of experiments were designed to observe the in vivo effect of regional hyperthermia on Dunning tumor growth for one month. The Dunning R3327 prostatic adenocarcinoma was chosen because it is reported to be an ideal animal model for the study of human prostatic tumors.

EXPERIMENTAL PROCEDURE

Twelve male Copenhagen rats were subcutaneously implanted with about 1 $mm^3$ viable Dunning R3327 prostate carcinoma specimens. The rats were then followed periodically until the tumors were measurable. When the tumor volume reached 0.5-2.0 $cm^3$, the hair overlying the tumor was shaved, the tumor was measured in three dimensions with precision calipers and the volume calculated.

The rats were divided into two equal groups and washed according to tumor size. Each group was anesthetized with intraperitoneal Nembutal (50mg/kg). All tumors were treated with topical iodine solution and the hyperthermia needles were disinfected with 70% ethanol. The treated group was prepared and the tungsten needle with the attached thermocouple was inserted into the tumor and heated. Hyperthermia was created by the resistive heating of a 22 gauge, 1.5 cm long tungsten needle by a DC power supply. The thermocouple, placed at the center of the needle, monitored the temperature and a specially constructed closed loop feed back circuit held the temperature constant ($+/-0.5°$ C.). The hyperthermia treatment continued for two hours after the needle temperature reached 46.5° C. Prior unpublished results of these experiments with 42.5, 44.5 and 46.5° C. hyperthermia treatment resulted in a significant delay of tumor growth and marked tumor necrosis without serious side effects. The experiments were, therefore, carried out using a temperature setting of 46.6° C. Two hyperthermia treatments, separated by a 48-hour interval, were administered. In the control group, the tungsten needle was inserted into the tumor, but was not heated.

After treatment, serial measurements of tumor volume and body weight were made twice a week for four weeks. On day 29 after final treatment all tumors were removed. Autopsy was performed in each rat for gross observation and pathological examination. Lung samples were obtained to search for metastatic lesions. The samples were fixed in formalin and processed by routine histological methods. All slides were stained with Hematoxylin and Eosin and evaluated by light microscopy.

Before treatment, there were no significant differences in tumor size between the two groups. After two hyperthermia therapies, the growth of tumor in the treated group was markedly delayed. From day 12 to day 22, the tumor size of the treated group was significantly less than that of the control group. The fourth week of measurement showed treated tumors growing faster than during the first three weeks.

From the first day of tumor measurement to day 22, the percent change of the mean value of the tumor size was substantial (227% less in treated than in control).

One week after the second treatment, the mean volume of tumor in the treated group was significantly less than that in the control group.

No other areas of injury were identified and no immediate mortality occurred, two rats died from lung metastases of the prostatic carcinoma on day 22. In the treated group, no lung metastases were found and no rats died before day 29.

Microscopic evaluation of the tumors included determination of the amount of solid or stratified pattern versus simple nonstratified glandular pattern, the mitotic rate, the size of the tumor made up by stroma and observed injuries, e.g. infarcts, vascular thrombosis, and hemorrhage. The hyperthermia treated tumors exhibited increased areas of solid or stratified morphology. The mitotic rate and the relative amount of stroma did not vary significantly from group to group. Infarcts, vascular thrombosis, stromal sclerosis, necrosis and organizing foci were typically present in the hyperthermia treated group. Hyperthermia treated tumors characteristically showed also increased areas of piled up cells with no lumen formation.

In this study, the action of initially applied hyperthermia and growth delay on the Dunning tumor model was studied over a period of one month. After two treatments of hyperthermia therapy within a time span of 48 hours, the growth of the Dunning tumor was delayed almost two weeks.

Although the 46.5° C. needle temperature was maintained for two hours, there were no deleterious effects on the total condition of the rat. This toleration of hyperthermia therapy may be related to the poor circulation in the prostatic tumor or its subcutaneous location. Changes in body weights (treated and control groups decreased 7% and 3%, respectively) were observed in both groups.

Two rats in the control group died from lung metastases on day 22 while no lung metastases were found among treated animals. However, it is not clear if hyperthermia therapy will prevent metastasis from prostatic tumor.

Using different temperatures (42 to 44° C.), other investigators have observed the importance of sequencing hyperthermia with additional treatment modalities. In the observation of treated tumors, regional necrosis was found for about one week after hyperthermia therapy. Additional treatment modalities could be considered in this time period. In the second week, some regional necrosis was absorbed, then the tumor growth gradually recovered. Beyond this time, some necrosis was maintained and continued to compromise the tumor. The important factor involved was tumor volume. Because a single needle size was employed regardless of tumor volume, the effect on a smaller tumor would be greater than that on a larger one.

Because thermotolerance with the development of heat resistant proteins may represent a clinical problem, especially in tumors treated at lower temperatures. A temperature of 46.5° C. was used by an interstitial technique, which has the possibility to raise temperatures to a degree overcoming these problems, without associated surrounding tissue damage. Other effects, as previously discussed, are related to blood flow and systemic temperature elevations.

DETAILED DESCRIPTION OF THE INVENTION

In order to create the necessary magnetic field strength to inductively heat thermoseeds, a commercially available power supply is utilized to power a specially designed coil. Both supply and coil may be watercooled if needed to control equipment temperature. In some instances, water cooling will be unnecessary.

The power supply in one preferred embodiment is 7.1 kw and utilizes a frequency of 115 kHz. The frequency may be in the range of 50 to 200 kHz, preferably between 80 and 120 kHz. In any event, the frequency must be below 500 kHz. The coil is 42 cm in diameter, 20 cm in length and consist of 10 turns of copper tubing. The coil may have, for example, an impedance of approximately 60 ohms at the operating frequency.

The power supply and coil produce a maximum magnetic field strength of from approximately 5 to 150 oersteds, preferably 10 to 100 oersteds on the axis at the edge of the coil. The axis of the coil is mounted vertically, with a plexiglass work table (e.g. seat or chair) covering the entire diameter. This field intensity creates a working volume 20 cm to 65 cm in diameter and 15 cm to 45 cm in height, centered about the coil axis and 4 cm above the uppermost coil winding. In the working field the space is of sufficient intensity to inductively heat the thermoseeds to the desired temperature. A reflector may be provided around the periphery and beneath the coil as a shield protection with the only exposed field being in an upward direction. The present invention may include a control panel with the necessary controls, switches, indicators and monitoring devices.

The seeds may be of any suitable metal or alloy that provides the previously described properties. Typical alloys include nickel/copper, platinum/copper, nickel/silicon, iron/manganese, and manganese/ferrite. Preferably, seeds of 70% nickel and 30% copper with a diameter of 1 mm are used. This alloy has a curie point temperature of 50° C. The curie point of each wire is determined by placing it in a small vial of approximately 5 cc of water. The vials are placed in the working space of the magnetic field and their temperature is measured by thermocouple every 5 minutes. The field is turned off during the temperature measurement to avoid interfering induced currents on the thermocouple leads. Seeds which attain 50+/−0.5° C. within 15 minutes of field activation are desirable. The heat produced by the alloy thermoseeds is proportional to the magnetic field intensity times the operating frequency, HF; this value for our system is $1.2 \times 10^8$ A/ms.

Subsequently, the following in vivo studies were carried out based on the prior experience using an interstitial technique.

Thirty-six male Copenhagen rats with subcutaneous Dunning prostate tumor sized between 0.7 to 1.5 cm³ on the right thigh, were divided into six groups.

Hyperthermia therapy (50° C. for 2 hr) was repeated after 48 hours in the first group and after one week in the second group. The third group was treated only once with hyperthermia. Each group had its own control group.

After treatment, the tumor as well as the body weight were measured twice a week for four weeks. On day 29, all rats were sacrificed. The lung and the tumor were removed and sent for pathological examination.

IN THE DRAWINGS

Figure 1:
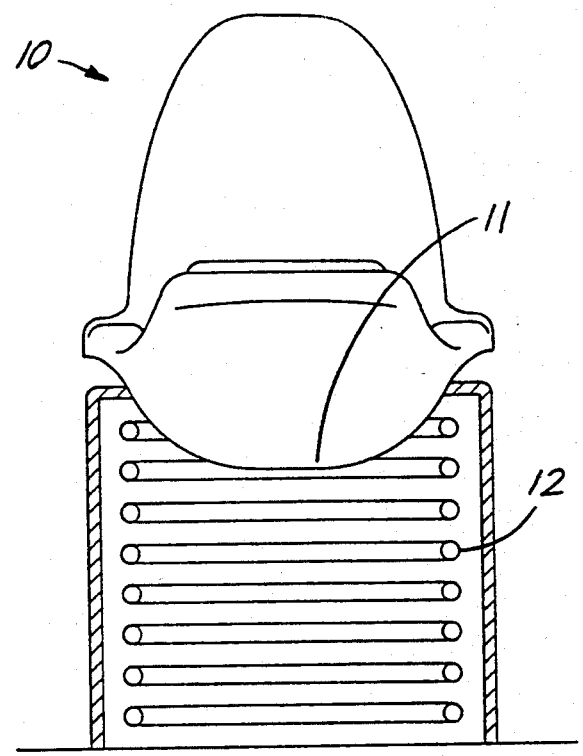
FIG. 1 is a front view of one embodiment of the present invention.
Figure 2:
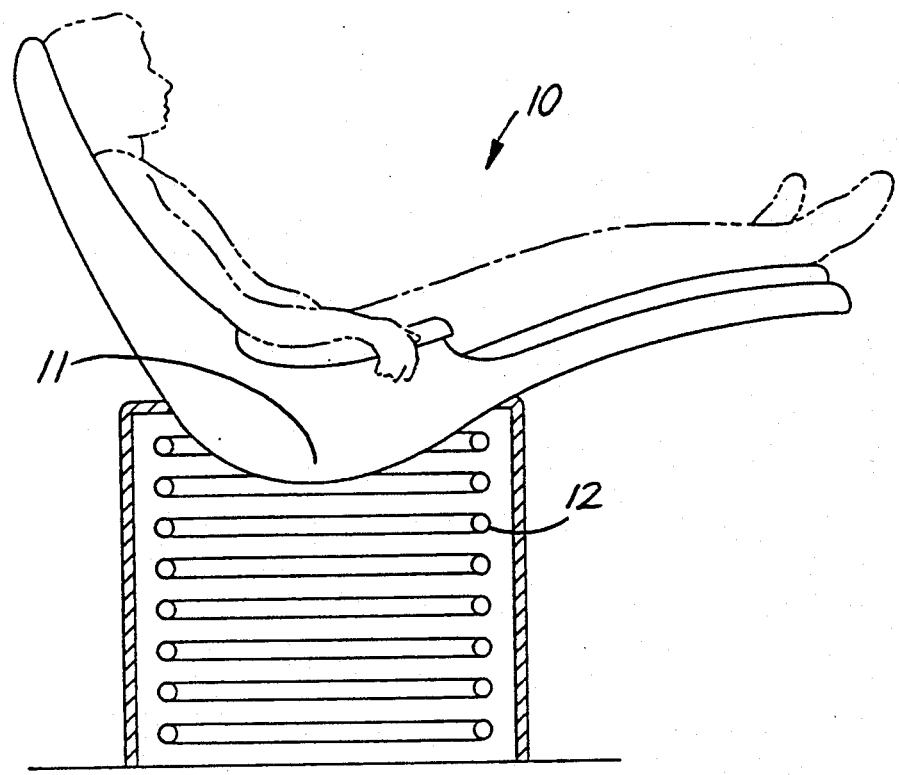
FIG. 2 is a side sectional view of the device of FIG. 1.
Figure 3:
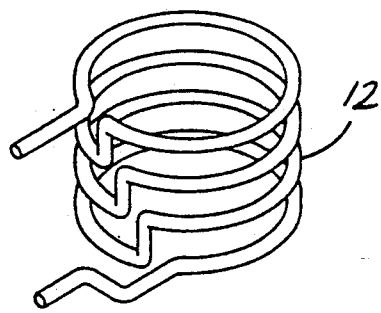
FIG. 3 shows a cylindrical coil of the present invention.
Figure 4:
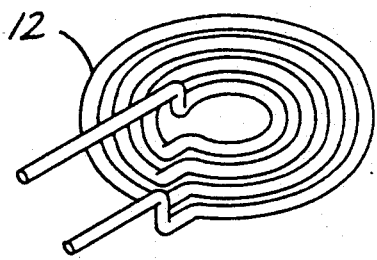
FIG. 4 shows a pancake coil of the present invention.

Preferred equipment for carrying out the present invention is shown in FIGS. 1 and 2. FIG. 1 shows a support 10 of the present invention including a platform 11 and a coil 12 disposed beneath the platform 11. The coil 12 may be constructed of copper tubing having a tube diameter of about 1 inch. The copper tubing may be connected to a self-contained water circulating system to control the temperature of the tubing. The platform 11 is contoured to require positioning of the patient to assure positioning of the tumor with the thermoseeds within the field of the coil during treatment. The coil, as shown in FIGS. 1 and 2 is a cylindrically shaped coil; however, other types of coils may be used such as a pancake coil (FIG. 4). Such coils may have from 5 to 15 turns. The cylindrical coil may typically be 40 cm in diameter and 30 cm in length. The pancake coil may typically be 30 cm in diameter and 15 cm in length. Alternatively, the coil may be a small portable coil and may be tightly wound coil with very little spacing between the turns. In this case, the coil may have from 50 to several hundred turns of fine conductor. The coil will usually be disposed in the seat or chair as shown in FIGS. 1 and 2. Alternatively, a smaller coil may be mounted on an arm which is moveable to center the coils' field on a given area of the body where a tumor is to be treated. Of course, all parts in the vicinity of the coil will be of a non-conducting material to avoid heating of such parts.

Figure 5:
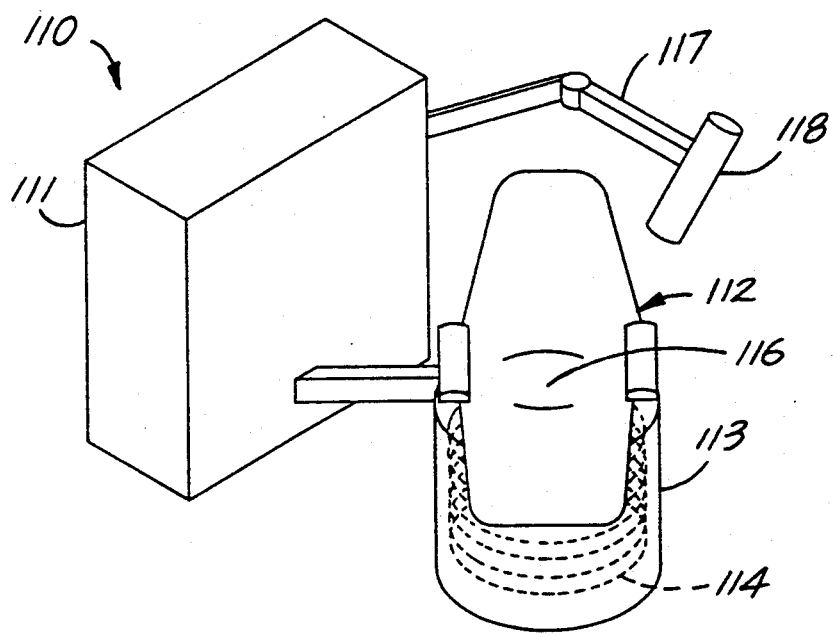
FIG. 5 is a perspective view of an embodiment of the present invention including a seat coil and an articulated arm coil.

Such a coil is illustrated in the device 110 of FIG. 5. Device 110 includes a control housing 111 which may contain the electrical components and controls as described. The device 110 includes a seat 112 which may be constructed similar to seat 10 of FIG. 1. Seat 112 has a seat housing 113, a coil 114 and a support platform 116. The coil 114 is in electrical contact with the components of housing 111. The device 110 has an articulated arm 117 which carries a coil 118. The coil 118 is suitable for treating tumors in any of various parts of the body.

Figure 6:
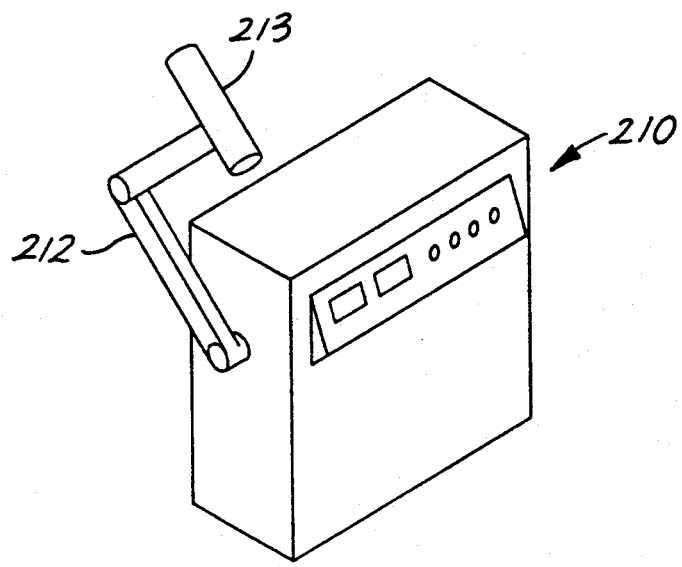
FIG. 6 is a perspective view of an embodiment of the present invention comprising an articulated arm coil.

A device 210 of the present invention is shown in FIG. 6. The device 210 includes a housing 211, an articulated arm 212 and a coil 213. The articulated arm 212 may be of any desired form such that it is capable of supporting the coil 213 in position adjacent a patients body for treatment of a tumor. The coil 213 may be moved to the desired location for treatment of a tumor. The housing 211 is portable and may be moved on its supporting wheels to a position adjacent to a patient's hospital bed for use. The housing 211 may carry the power supply of a type as previously described. The power supply may provide current at a frequency of from 50 to 200 kHz to produce a magnetic field of between 50 and 150 oersteds.

While preferred embodiments are disclosed, various modifications ma be made without departing from the broader scope of the present invention.

What is claimed is:

1. An apparatus for the treatment of prostate cancer, said apparatus comprising a platform for the support of a person having a prostate tumor and a coil formed of electrically conductive tubing, said platform having a seat with an upper surface, said upper surface being positioned within 4 cm of the uppermost turn of said coil, said upper surface being contoured for reproducibly receiving the buttocks of a person in alignment with the axis of said coil.

2. The apparatus of claim 1 wherein said apparatus further comprises a power source, said power source and said coil being capable of producing a magnetic field strength of 5 to 150 oersteds.

3. The apparatus of claim 2 wherein said coil has a diameter of from generally 20 cm to 65 cm and a length of generally 15 cm to 45 cm.

4. The apparatus of claim 3 wherein said coil is of copper tubing and has generally 50 turns.

5. The apparatus of claim 4 wherein said coil has a working field volume of generally 20 cm in diameter and generally 15 cm in height.

6. The apparatus of claim 5 wherein said platform is a chair-like structure on which the person may be seated during treatment.

7. The apparatus of claim 4 wherein said coil has a working field that extends about 20 cm above the uppermost turn of the coil.

8. The apparatus of claim 6 wherein said platform is concave and extends downwardly into the center of the diameter of the coil, whereby the seat upper surface is positioned well within the field of the coil during treatment.

* * * * *

UNITED STATES PATENT AND TRADEMARK OFFICE
CERTIFICATE OF CORRECTION

PATENT NO. : 5,197,940

DATED : March 30, 1993

INVENTOR(S) : CHESTER E. SIEVERT, JR., ROBERT D. TUCKER, STEFEN LOENING

It is certified that error appears in the above-identified patent and that said Letters Patent is hereby corrected as shown below:

Col. 11, line 15, delete "50 turns.", insert --10 turns.--

Signed and Sealed this

Thirtieth Day of November, 1993

Attest:

BRUCE LEHMAN

Attesting Officer

Commissioner of Patents and Trademarks